US00PP07899P

United States Patent [19]

van Andel

[11] Patent Number: Plant 7,899

[45] Date of Patent: Jun. 30, 1992

[54] CARNATION NAMED STAPISOU

[75] Inventor: Jacob van Andel, Aalsmeer, Netherlands

[73] Assignee: Van Staaveren B.V., Aalsmeer, Netherlands

[21] Appl. No.: 604,529

[22] Filed: Oct. 29, 1990

[51] Int. Cl.[5] ..... A01H 5/00

[52] U.S. Cl. ..... Plt./71

[58] Field of Search ..... Plt./71, 72

*Primary Examiner*—James R. Feyrer

*Attorney, Agent, or Firm*—Charles W. Rummler

[57] ABSTRACT

A new and original spray carnation variety particularly distinguished by its pink-colored blossoms, which are borne on strong, upright stems. This carnation blooms continuously during the Spring, Summer, and Fall blooming periods.

1 Drawing Sheet

BACKGROUND OF THE NEW PLANT

This new carnation cultivar originated as a Hybrid Seedling developed by me in 1985 at our nursery in Aalsmeer, Holland by crossing two varieties selected from our collection of carnations maintained for breeding purposes as Aalsmeer. This particular seedling was selected for propagation because of its pink color, its long stem, and the overall high quality of the plant growth. Asexual propagation of this selected plant was done by means of cuttings under my direction at Aalsmeer; and propagation of this new plant by cuttings was continued through successive generations to determine whether the novel characteristics of the selected seedling would be retained from generation to generation and its homogeneity could be assured.

This proved to be successful and this new mini-spray carnation variety is now being propagated at Aalsmeer.

DESCRIPTION OF THE DRAWING

My new spray carnation cultivar is illustrated by the accompanying full-color photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new spray carnation variety based upon observation of plants grown in greenhouse as well as outdoors at Aalsmeer and blooming during the current year. The color designations stated herein are according to the R.H.S. COLOUR CHART published by The Royal Horticultural Society of London, England.

THE PLANT

Origin: Seedling.

Parentage:

*Seed parent.*—84606-1C (unpatented).

*Pollen parent.*—Stadonros (unpatented).

Classification:

*Botanic.*—Dianthus Caryophyllus.

*Commercial.*—Spray carnation.

Form: Strong, upright bush.

Height: In average, about 100 cm.

Main stem:

*Length.*—In average, about 50 cm.

*Growth.*—Vigorous, spreading and strong.

*Branching character.*—One shoot per inter-node.

Foliage:

*Number of leaves.*—Varies depending upon season and length of day.

*Leaf size.*—About 13 cm long and 1.2 cm wide at the fifth node.

*Leaf shape.*—Pointed and curled. Margins: Entire. Texture: Leathery. Color: Upper side: Gray-green. Under side: Gray-green.

THE BUD

Size: Medium.

*Diameter.*—Averaging about 10 mm.

*Length.*—Averaging about 20 mm.

Shape: Ovoid.

Calyx:

*Shape.*—Funnel-shaped.

*Size.*—Averaging about 15 mm in width and 25 mm in length.

*Splitting.*—The calyx does not split.

*Aspect.*—Smooth.

Flower stem:

*Character.*—Erect.

*Length.*—In average, 50 cm.

THE FLOWER

Blooming habit: Continuous.

Size of flower: Small.

*Diameter.*—Averaging about 40 mm.

*Depth.*—Averaging between 15 and 20 mm.

Borne: Raceme.

Shape:

*When first opening.*—High center.

*When mature.*—Dome shaped.

Petalage:

*Arrangement.*—Imbricated.

*Form.*—Ovate.

*Margin type.*—Serrate.

*Texture.*—Smooth.

*Appearance.*—Velvety.

*Number of petals.*—About 20-25.

*Color.*—Both outer and inside petals: Body: 49 A/B. Base: 49 A/B. Reverse side: 59 A/B.

Flower stem:

*Length.*—Averaging about 50 cm.

*Character.*—Strong and upright.

Discoloration:

*After full bloom.*—No discoloration.

Fragrance: Slight.

Persistence: The flowers hang on and dry.

Lasting quality: Averaging about 10 days as a cut flower and 18 days on the plant.

REPRODUCTIVE ORGANS

Stamens:

*Number.*—Normal.

*Arrangement.*—Petaloid.

*Anthers.*—Size: Small. Color: White.

*Filaments.*—Length: 30 mm. Color: White.

*Pollen.*—Color: Gray-white, if present.

Pistils:

*Number.*—1.

*Styles.*—Length: About 20 mm. Color: White.

*Stigmas.*—Color: White.

Characteristics of ovaries: Ovoid.

FRUIT

Fertility: The fruit is fertile.

Shape: Ovoid.

Color at maturity: Light brown.

I claim:

1. The new and distinctive spray carnation plant, substantially as herein shown and described, particularly characterized by its pink-colored flowers, which are produced continuously on strong, upright stems of a vigorously growing bush.

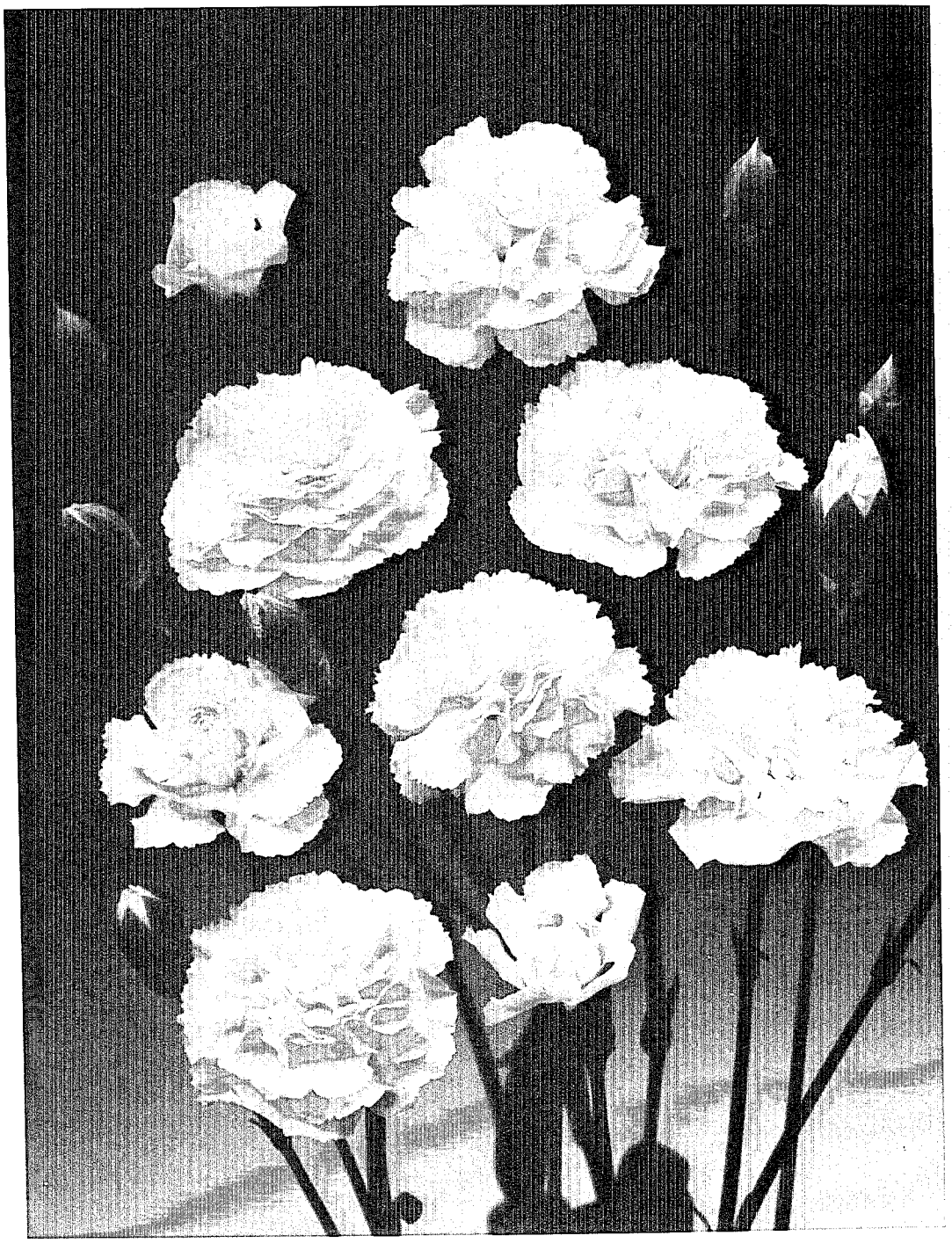

* * * * *